(12) United States Patent
Shimada et al.

(10) Patent No.: US 7,278,979 B2
(45) Date of Patent: Oct. 9, 2007

(54) WALKING ASSISTANCE DEVICE HAVING A PELVIS SUPPORT MEMBER THAT IS EASY TO WEAR

(75) Inventors: Kei Shimada, Wako (JP); Takashi Hirata, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 281 days.

(21) Appl. No.: 11/215,402

(22) Filed: Aug. 30, 2005

(65) Prior Publication Data

US 2006/0052731 A1    Mar. 9, 2006

(30) Foreign Application Priority Data

| Sep. 7, 2004 | (JP) | ............................. 2004-259670 |
| Sep. 7, 2004 | (JP) | ............................. 2004-260072 |
| Sep. 22, 2004 | (JP) | ............................. 2004-274345 |

(51) Int. Cl.
*A61F 5/00* (2006.01)

(52) U.S. Cl. .............................. 602/16; 602/23; 482/51

(58) Field of Classification Search .................... 602/5, 602/16, 23, 24, 26, 27; 482/51
See application file for complete search history.

(56) References Cited

U.S. PATENT DOCUMENTS 4,557,257 A * 12/1985 Fernandez et al. .............. 602/5
4,872,665 A * 10/1989 Chareire ....................... 482/51
4,969,452 A * 11/1990 Petrofsky et al. ............. 602/16
5,658,242 A * 8/1997 McKay et al. ................ 602/16
5,961,476 A * 10/1999 Betto et al. ................... 602/16

FOREIGN PATENT DOCUMENTS

JP          2002-301124          10/2005

* cited by examiner

*Primary Examiner*—Michael A. Brown
(74) *Attorney, Agent, or Firm*—Rankin, Hill, Porter & Clark LLP

(57) ABSTRACT

In a walking assistance device that includes a pelvis support member adapted to be worn around a hip of a wearer and at least one actuator having a base end mounted on the pelvis support member and a free end engaging a thigh of the wearer, the pelvis support member comprises a substantially U-shaped base portion having a relatively high rigidity and adapted to be worn around the hip of the wearer and a pair of flaps having a relatively high resilient flexibility and extending from either end of the base portion toward each other; free ends of the flaps defining a gap smaller than a width of the hip of the wearer. Therefore, the wearer can bend the flaps outward so as to define a gap wide enough to pass the hip of the wearer, and once the wearer is fit into the pelvis support member, the flaps are allowed to return to their original shape owing to their resiliency, and engage the front side part of the hip of the wearer. The base portion, on the other hand, may be given with an adequate rigidity to support the actuator without any problem.

8 Claims, 7 Drawing Sheets

WALKING ASSISTANCE DEVICE HAVING A PELVIS SUPPORT MEMBER THAT IS EASY TO WEAR

TECHNICAL FIELD

The present invention relates to a walking assistance device that includes a pelvis support member adapted to be worn around a hip of a wearer and at least one actuator having a base end mounted on the pelvis support member and a free end engaging a thigh of the wearer.

BACKGROUND OF THE INVENTION

Various muscle assistance devices have been proposed as can be found in Japanese patent laid open publication No. 2002-301124, for instance, for the purpose of providing an assisting force to the movement of the leg by using a toque actuator consisting of an electric motor or the like attached to a side part of the hip or knee joint. For instance, such a muscle assistance device enables a person caring a bedridden person to produce a force of the leg which is substantially greater than that the person is normally capable of producing or a person having a walking impediment owing to aging or the like to walk on his or her feet.

Such a conventional walking assistance device is typically provided with an abdomen support member that is wrapped around the abdomen of the wearer and is kept tightly around the abdomen by using Velcro (trademark) tape or a fastening belt in a detachable manner.

However, if the abdomen support member is formed as a cylindrical member like a corset, as it is typically made of relatively rigid plastic material, a considerable effort is required to open one side of the cylindrical member and fit the torso of the wearer into the interior of the cylindrical member. The wearing of the abdomen support member may be facilitated by forming the abdomen support member from more flexible material. However, the abdomen support member is required to have a certain rigidity for the purpose of supporting the actuator. If the abdomen support member lacks a required rigidity, the abdomen support member is unable to support the reaction force of the actuator, and a desired output of the actuator cannot be obtained. Also, such a reaction force causes the actuator to move about with respect to the body of the wearer, and it becomes impossible to control the operation of the actuator in a desired manner.

Furthermore, a human abdomen lacks a skeletal support, and is not able to support a load without causing uncomfortable pressure to the wearer. If the tightness of the abdomen support member is reduced, it would not be able to support the walking assistance device or the reaction of the actuator. Also, the abdomen support member constrains the human abdomen to such an extent that the wearer is hampered from stooping forward, twisting or otherwise moving the body. Also, the width of the human abdomen can vary to such an extent that the walking assistance device of a single size can fit only a small number of wearers and walking assistance devices of a large number of different sizes must be prepared to meet the needs of the wearers of different builds. This leads to an increase in the cost.

Also, as such a walking assistance device sometimes has to be worn unassisted by a disabled person having a limited muscle power, it is highly important that the walking device is light in weight and easy to handle. Additionally, the walking device should be comfortable to wear, and should not unduly hamper the movement of the wearer.

BRIEF SUMMARY OF THE INVENTION

In view of such problems of the prior art, a primary object of the present invention is to provide a walking assistance device that can be firmly attached to the wearer without causing any undue discomfort to the wearer.

A second object of the present invention is to provide a walking assistance device that is provided with a body support member that is given with a high rigidity to favorably support the reaction force of an actuator and is easy to wear at the same time.

A third object of the present invention is to provide a walking assistance device which is light in weight and easy to handle.

A fourth object of the present invention is to provide a walking assistance device that would not unduly hamper the body movement of the wearer.

To achieve at least some of such objects, the present invention provides a walking assistance device that includes a pelvis support member adapted to be worn around a hip of a wearer and at least one actuator having a base end mounted on the pelvis support member and a free end engaging a thigh of the wearer, wherein: the pelvis support member comprises a substantially U-shaped base portion having a relatively high rigidity and adapted to be worn around the hip of the wearer and a pair of flaps having a relatively high resilient flexibility and extending from either end of the base portion toward each other; free ends of the flaps defining a gap smaller than a width of the hip of the wearer.

Therefore, the wearer can bend the flaps outward so as to define a gap wide enough to pass the hip of the wearer, and once the wearer is fit into the pelvis support member, the flaps are allowed to return to their original shape owing to their resiliency, and engage the front side part of the hip of the wearer. The base portion, on the other hand, may be given with an adequate rigidity to support the actuator without any problem.

The base portion and flaps may be made of a single piece fiber-reinforced composite member, or, alternatively, the flaps may be made separately from the base portion and attached thereto by using a fastener or bonding agent.

If desired, the base portion may be provided with at least one slide guide that allows a lengthwise adjustment of the base portion and a locking arrangement for securing an adjusted state of the slide guide so that a desired fit may be achieved without regard to the build of the wearer. According to such an arrangement, a walking assistance device of a single size can fit a large number of people, and this reduces the cost by eliminating the need to manufacture and/or stock walking assistance devices of a large number of different sizes. In such a case, preferably, the slide guide further includes a ratchet mechanism for selectively pulling together two ends of the slide guide in an incremental manner.

Because the base portion is provided with a high rigidity, a handle grip may be safely provided in the base portion for holding the walking assistance device in a suspended state. Thereby, the handling of the walking assistance device is substantially improved.

For the comfort of the wearer and secure support of the walking assistance device on the wearer, the pelvis support member should be adapted to engage the wearer at five points that include a back side of a sacroiliac joint (joint between a vertebrae and a pelvic bone), crest portions of right and left iliac regions (lateral side ends of the pelvic bone), and right and left spina iliac regions (front ends of the pelvic bone) of the wearer. A cushioning pad may be interposed between at least one of the five points and the wearer so that the comfort of the wearer may be improved, and a favorable fit may be achieved for wearers of various builds.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
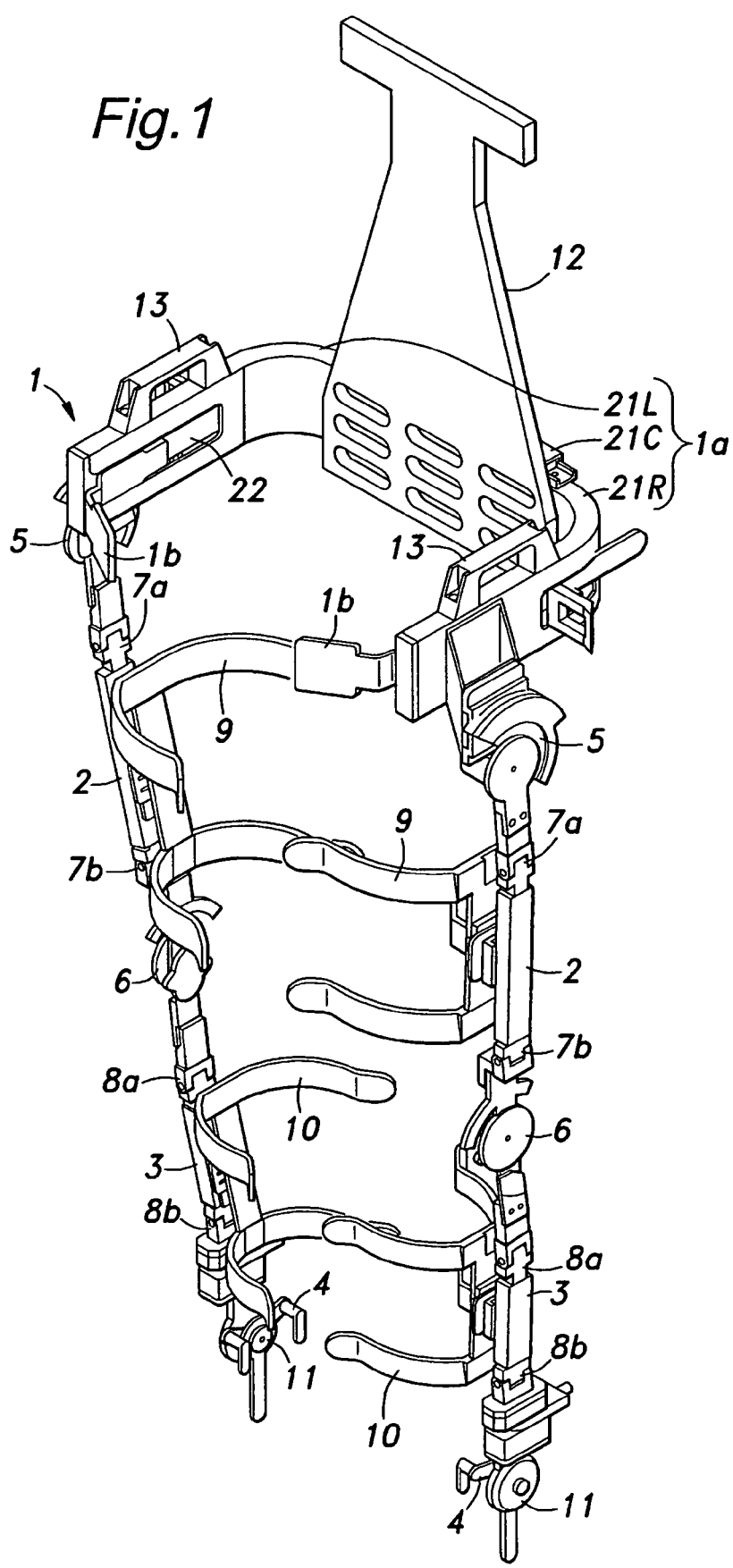
FIG. 1 is an overall perspective view of the walking assistance device embodying the present invention.
Figure 2:
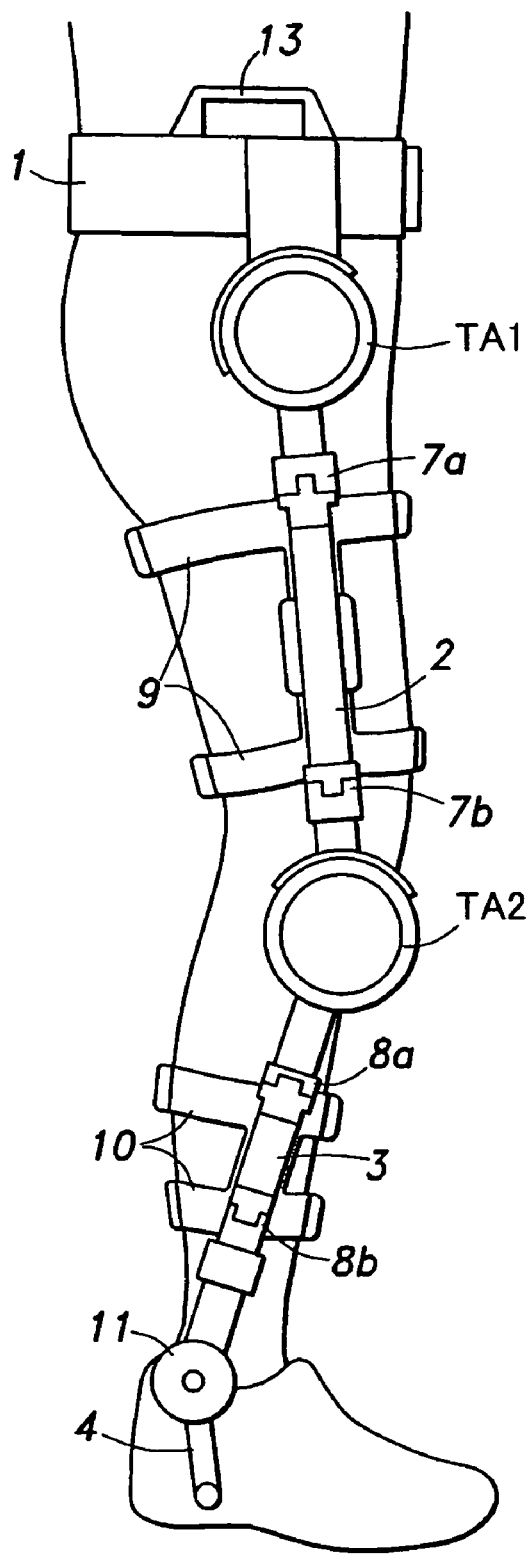
FIG. 2 is a side view showing the walking assistance device as worn by a person.

FIG. 1 is an overall perspective view of an exoskeltal walking assistance device embodying the present invention, and FIG. 2 is a side view showing the walking assistance device when worn by a user. As shown in FIG. 1, the walking assistance device comprises a pelvis support member 1 adapted to be worn on the pelvis of the user, a thigh support member 2 which is vertically elongated so as to be placed on the outer side part of each thigh of the user, a leg support member 3 adapted to be placed on the outer part of each leg of the user, and a foot support member 4 adapted to be engaged by the shoe worn on each foot of the user. The "thigh" as used herein means a part of the limb extending between the hip joint and knee joint, and the "leg" as used herein means a part of the limb extending between the knee joint and ankle.

The pelvis support member 1 includes a base portion 1a made of a relatively rigid material and provided with the shape of letter-U as seen in plan view and a pair of flaps 1b each extending from a corresponding open front end of the base portion 1a and made of a resilient thin plate member so that the pelvis support member 1 as a whole presents the shape of letter-C including an open central front part. The gap between the flaps 1b is typically smaller than the width of the hip of the wearer, but the resiliency of the flaps 1b allows the hip of the wearer to be passed through the gap between the flaps 1b and into the interior of the pelvis support member 1.

The base portion 1a is provided with a relatively high rigidity as it is required to support the rest of the walking assistance device. In particular, because the base portion 1a is required to support the actuators for actuating the thigh support members relative to the pelvis support member 1 as will be described hereinafter, it is required to have an adequate mechanical strength and rigidity to be able to keep the actuators at the fixed positions. Also, the base portion 1a is required to have an adequate mechanical strength and rigidity to withstand the reaction forces which the actuators produce.

A middle part of the base portion 1a is adapted to be extended and retracted laterally as will be described hereinafter while the flaps 1b are adapted to be extended and retracted in the fore-and-aft direction so as to accommodate the variable build of the wearer. The adjusted state of the base portion 1a can be immovably fixed by using suitable securing means such as threaded bolts.

The front end of each side portion of the pelvis support member 1 is provided with a pelvis actuator base 5 for mounting a first torque actuator TA1 (FIG. 2) for applying a torque to the pelvic joint of the corresponding side. The output end of the first torque actuator TA1 is connected to the upper end of the thigh support member 2. The lower end of each thigh support member 2 is provided with a knee actuator base 6 for mounting a second torque actuator TA2 (FIG. 2) for applying a torque to the knee joint of the corresponding side. The output end of the second torque actuator TA2 is connected to the upper end of the leg support member 3.

The thigh support member 2 is joined to the output end of the first torque actuator TA1 and knee actuator base 6, in each case, in an articulated manner via a hinge 7a, 7b having a hinge axis extending in the fore-and-aft direction. The leg support member 3 is joined to the output end of the second torque actuator TA2 and foot support member 4, in each case, in an articulated manner via a hinge 8a, 8b having a hinge axis extending in the fore-and-aft direction. The thigh support member 2 and leg support member 3 are each adapted to be slidably extended and retracted so as to accommodate the variable stature of the wearer. The adjusted lengths of the thigh support member 2 and leg support member 3 can be immovably fixed by using suitable securing means such as threaded bolts.

Each of the torque actuators TA1, TA2 mounted on the actuator bases 5 and 6, respectively, consists of an electric motor fitted with a clutch and a reduction gear, and the motor housings thereof are mounted on the corresponding actuator bases 5,6 provided on the pelvis support member 1 and the lower end of the thigh support member 2, respectively, while the output ends or rotors thereof are fixedly connected to the upper ends of the thigh support member 2 and leg support member 3, respectively. Thereby, an assisting torque corresponding to the intended movement of each of the hip joint (the joint between the pelvis support member 1 and thigh support member 2) and knee joint (the joint between the thigh support member 2 and leg support member 3) is produced. The torque actuators TA1, TA2 may be attached to the corresponding actuator bases 5 and 6 by using fastening means that can be repeatedly fastened and unfastened so that the maintenance and repair of the torque actuators may be facilitated.

Each thigh support member 2 is provided with a pair of cross members 9 each made of a C-shaped resilient member in a vertically spaced manner. The cross members 9 are jointly mounted at a suitable point on the thigh support member 2 in a vertically slidable manner, and adapted to attach the thigh support member 2 to the thigh of the wearer. Each leg support member 3 is similarly provided with a pair of cross members 10 each made of a C-shaped resilient member in a vertically spaced manner. The cross members 10 are jointly mounted at a suitable point on the leg support member 3 in a vertically slidable manner, and are adapted to attach the leg support member 3 to the leg of the wearer.

The joint between each leg support member 3 and corresponding foot support member 4 is rotatable around a laterally extending axis so as to accommodate the normal movement of the ankle.

To a central part of the pelvis support member 1 is attached a back plate 12 for mounting auxiliary equipment not shown in the drawings. For instance, a control circuit and a battery are mounted on the back plate 12.

A handle grip 13 is formed on the upper surface of each side portion of the base portion 1a of the pelvis support member 1 for allowing the entire walking assistance device to be held by hands in a suspended state. If desired, the handle grip may simply consist of an opening provided in the base portion or a separate member that can be detachably engaged to the base portion 1a when desired.

Figure 3:
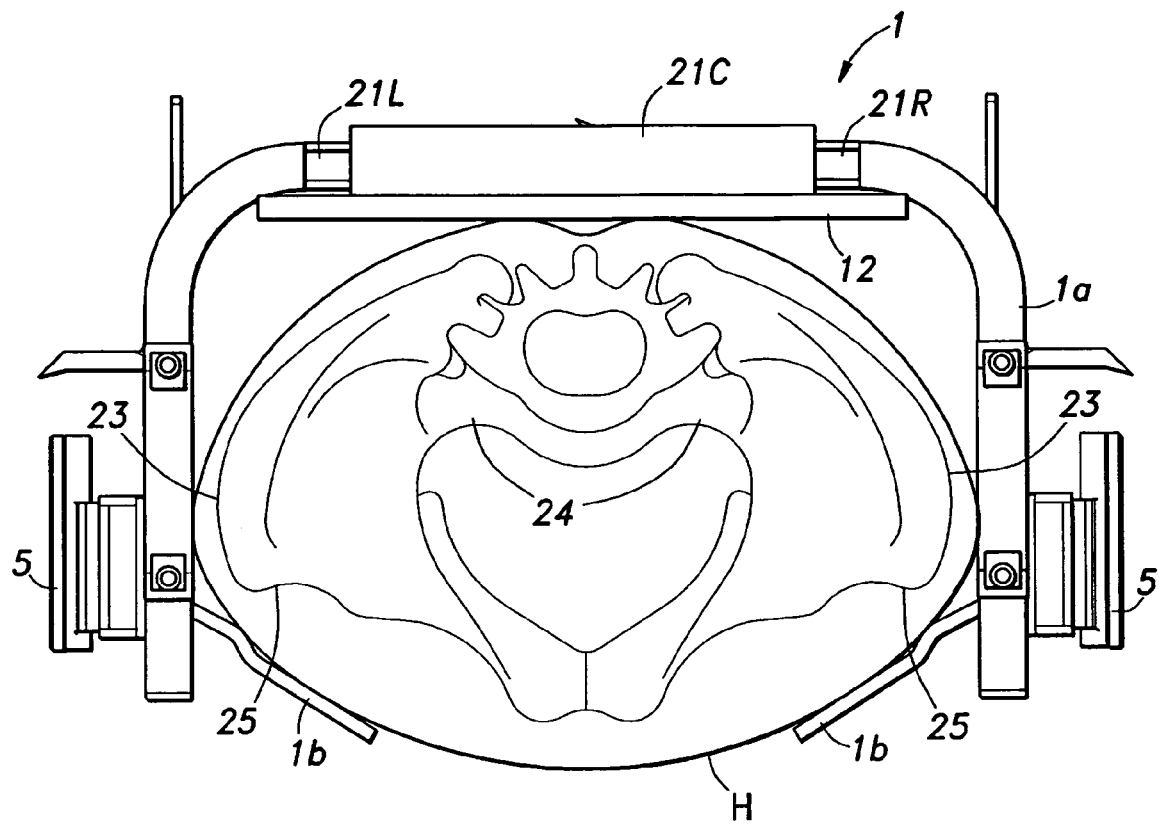
FIG. 3 is a plan view of the pelvis support member with the wearer shown in cross section.

As best illustrated in FIG. 3, the base portion 1a consists of left portion 21L and right portion 21R each shaped as a letter-L, and an I-shaped central portion 21C integrally attached to the back plate 12, and the left portion 21L and right portion 21R are each engaged with the central portion 21c at their opposing ends so as to be laterally slidable relative to each other. The right and left flaps 1b are each attached to the front end of the corresponding left portion 21L or right portion 21R, as the case may be, via a slide guide 22 (FIG. 1) so as to be slidable in the fore-and-aft direction. Therefore, by sliding the left portion 21L and right portion 21R of the base portion 1a relative to the central portion 21c, it is possible to adjust the gap between the two flaps 1a when wearing the pelvis support member 1 and, once the pelvis support member 1 is worn, the inner lateral width of the base portion 1a. Also, the inner fore-and-aft width of the base portion 1a can be adjusted by moving the side flaps 1b relative to the right and left portion 21L and 21R portions by using the slide guides 22.

Figure 4:
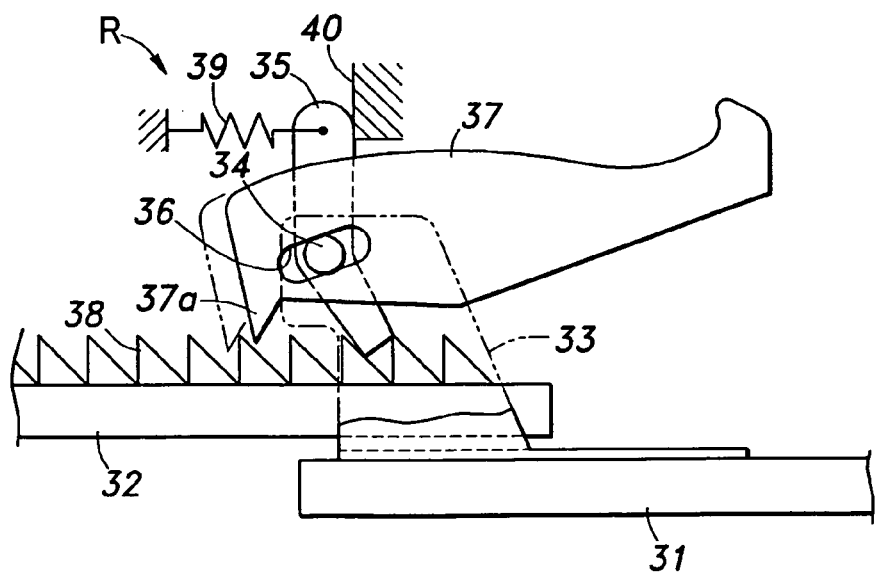
FIG. 4 is a schematic view of the ratchet mechanism for the slide guide of the base portion.
Figure 5:
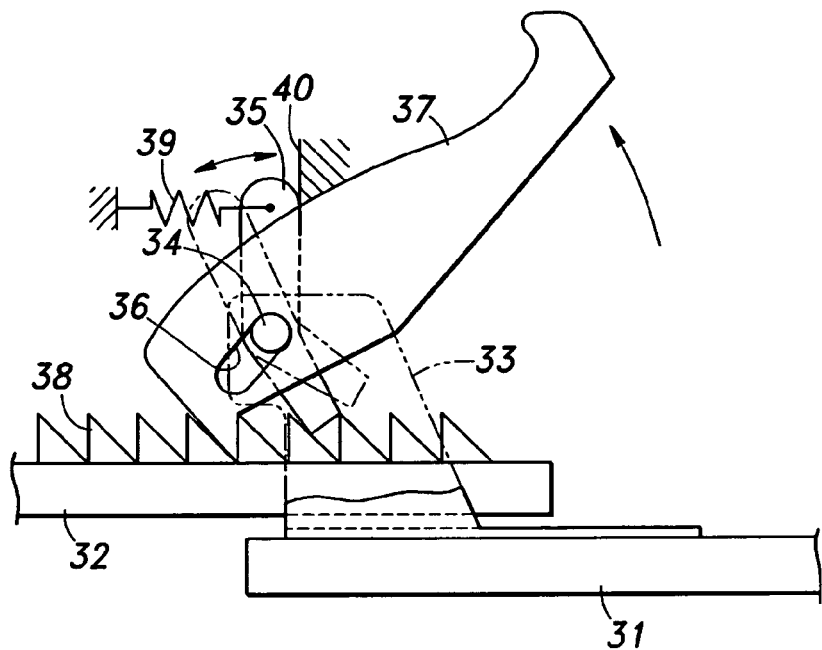
FIG. 5 is a view similar to FIG. 4 showing the adjusting movement of the ratchet lever.

The adjusted state of the right and left portion 21L and 21R can be fixed relative to the central portion 21c by using a locking mechanism or a ratchet mechanism R incorporated in each of the slidable arrangements in the base portion 1a and schematically illustrated in FIGS. 4 and 5. The ratchet mechanism R includes a first member 31, a second member 32 retained by the first member 33 so as to be slidable relatively to each other, a ratchet pawl 35 pivotally attached to the first member 31 via a bracket 33 formed in the first member 31 and a pin 34 passed into the bracket 34, a ratchet lever 37 provided with a slanted slot 36 receiving the pin 34 therein, and a ratchet gear teeth 38 formed in the second member 32. The ratchet teeth 38 are saw-tooth shaped, and are each provided with a substantially vertical left edge and a slanted right edge as illustrated in FIG. 4.

The ratchet lever 37 is rotatable around the pin 34 and is also freely moveable to the extent permitted by the engagement between the pin 34 and slot 36. The ratchet pawl 35 is normally urged by a spring member 39 into engagement with one of the ratchet gear teeth 38 or more particularly the vertical edge of the ratchet gear tooth 38.

FIG. 4 shows an early phase of engagement between the pawl 35 and teeth 38. When the first and second members 31 and 32 are extended relatively to each other, the ratchet pawl 35 is engaged by the vertical edge of one of the teeth 38 and is turned in clockwise direction until it abuts a stopper 40, and once the ratchet pawl 35 has abutted the stopper 40 and is prevented from any further clockwise rotation, the relatively extending movement between the first and second members 31 and 32 is prevented. If the ratchet lever 37 is slightly turned in counterclockwise direction so as to cause a projection 37a of the ratchet lever 37 to push one of the teeth 38 rightward as shown in FIG. 5, the second member 32 is moved toward the first member 31, and the ratchet pawl 35 is allowed to ride over the slanted edge of the corresponding ratchet tooth 38 against the spring force of the spring member 39. If the counterclockwise rotation of the ratchet lever 37 is effected until the ratchet pawl 35 goes over the top of the tooth 38, the ratchet pawl 35 will be allowed to advance relatively to the second member 32 by one tooth. By thus repeating the rocking movement of the ratchet lever 37 by a required number of times, it is possible to advance the ratchet pawl 35 from one tooth to another until the second member 32 retracts relatively to the first member 31 by a desired distance.

This ratchet mechanism R can be released by disengaging the ratchet pawl 38 from the tooth, and retaining the released ratchet pawl 38 at a disengaged position. Thereby, the first and second members 31 and 32 can be extended retracted at will without being hindered by the ratchet mechanism R.

By providing such a lock/ratchet mechanism between the right portion 21R and central portion 21c, between the left portion 21L and central portion 21c, between the left flap 1b and left portion 21L, and between the right flap 1b and right portion 21R, it is possible to adjust the width of the base portion 1a at will. If desired, such a ratchet mechanism may be provided only in selected parts instead of providing the ratchet mechanism R in each and every one of such locations.

However, it should be noted that such slide guides and ratchet mechanisms are purely optional according to the broad concept of the present invention. Even with slide guides, owing to the use of the resilient flaps 1b, the walking assistance device of the present invention can be adapted to wearers of various sizes.

How this walking assistance device can be worn is now described in the following. First of all, the lateral width and fore-and-aft width of the base portion 1a are suitably adjusted that the pelvic part of the wearer may be passed between the gap between the two flaps 1b and easily received inside the base portion 1a. The wearer or the person assisting the wearer may conveniently hold the walking assistance device by holding the gripping handles 13 by hands. Once the back side of the pelvic part of the wearer is pressed against the back plate 12, the lateral width and fore-and-aft width of the base portion 1a are suitably adjusted by using the ratchet mechanisms described above and provided in the suitable parts of the base portion 1a. A desired fit can be achieved by manipulating the ratchet mechanisms and securing them at the desired positions by using the locking mechanisms.

The walking assistance device is worn by the wearer in such a manner that the U-shaped base portion 1a engages the part of the pelvic portion of the wearer H extending from the crest portions of the right and left iliac regions (the lateral side ends of the pelvis) 23 to the back side of the sacroiliac joint (joint between the vertebrae and pelvic bone) 24, and the right and left flap portions 1b oppose the right and left spina iliac regions (front ends of the pelvic bone) 25 of the wearer H. Thereby, the walking assistance device can be properly positioned relative to the pelvic bone, and is favorably supported thereby.

Then, the cross members 9 and 10 for supporting the thigh and leg, respectively, are pulled open, and are fitted on the thigh and leg of the wearer H, respectively, from laterally outside. Thereby, the thigh support member 2 and leg support member 3 are placed on the thigh and leg of the wearer H. At this time, the two clutches of the torque actuator TA1 and TA2 should be disengaged so that the walking assistance device may be worn without regard to the posture of the wearer. For instance, the wearer may sit in a chair while wearing the walking assistance device additionally taking advantage of the hinges 7a, 7b, 8a and 8b provided in the end portions of the support members 2 and 3 that allow the support members to be flexed outwardly.

Because the cross members 9 and 10 are slidable relative to the corresponding support members 2 and 3, the relative movements between the thigh and thigh support member 2 and between the leg and left support member 3 are favorably accommodated, and there would be no undesired friction between the thigh and thigh support member 2 or between the leg and left support member 3 so that the wearer would not experience any discomfort even when the level of exertion by the wearer is relatively high.

Figure 6A:
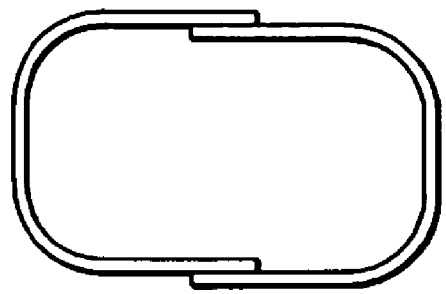
FIGS. 6a to 6c are simplified plan views showing different embodiments of the arrangement for the base portion.
Figure 6B:
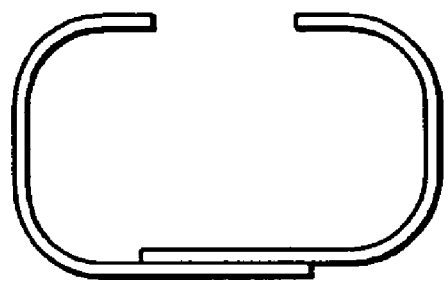
Figure 6C:
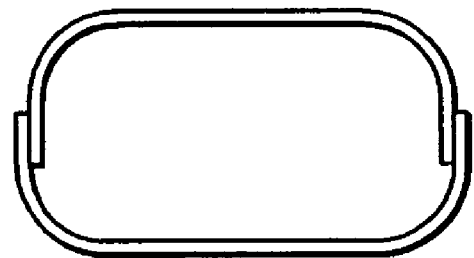

The base portion 1a was provided with a C-shaped structure and a pair of flaps 1b on either open end of the C-shaped structure. However, other arrangements are also possible. FIG. 6a shows a pair of U-shaped members that can be combined with each other by opposing their open ends laterally toward each other and defining a substantially enclosed structure. Alternatively, the front end may not be fully closed, and the base portion 1a may be provided with an open front end as illustrated in FIG. 6b. Otherwise, this embodiment is similar to that shown in FIG. 6a. Also, a pair of U-shaped members may be combined in such a manner that the open ends oppose each other in the fore-and-aft direction and define a substantially enclosed structure as illustrated in FIG. 6c.

Figure 7:
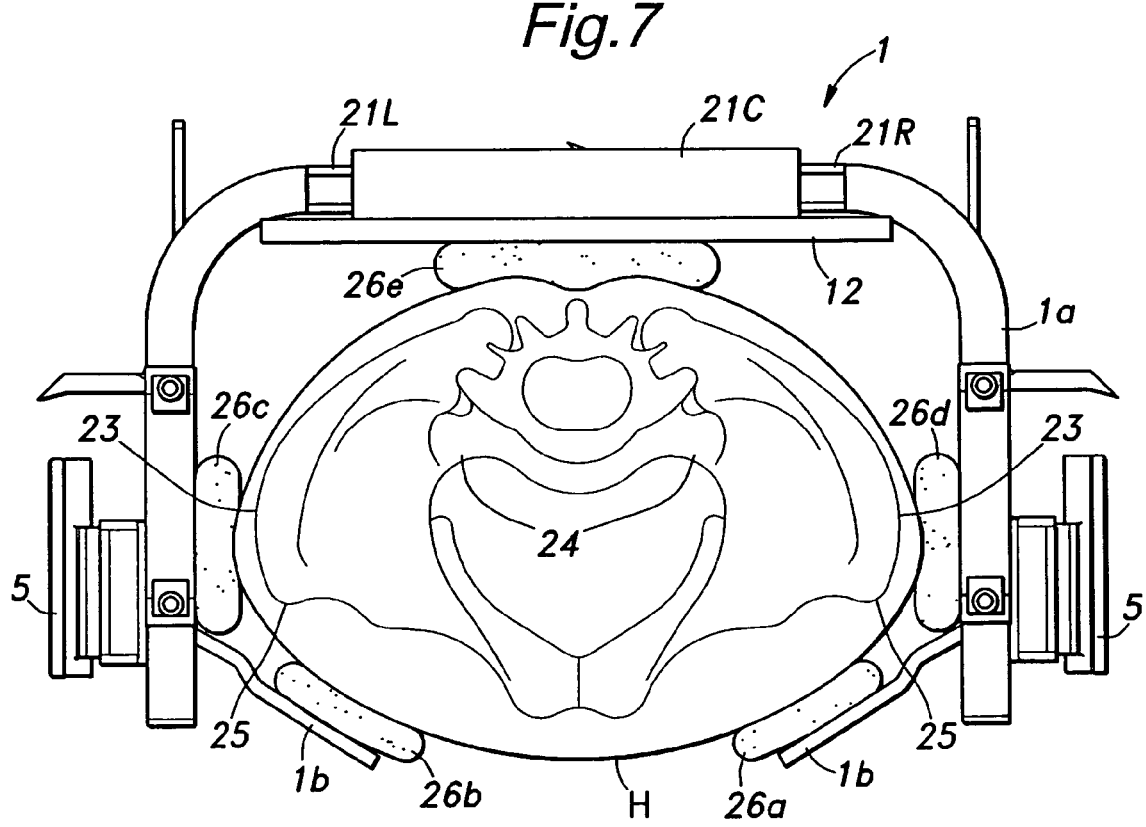
FIG. 7 is a view similar to FIG. 3 showing a modified embodiment of the present invention.

To improve the comfort of the wearer a plurality of separate cushioning pads 26a-26e may be provided in suitable parts of the base portion 1a and/or flaps 1b as illustrated in FIG. 7. In the illustrated embodiment, the cushioning pads are provided five locations that correspond to a back side of a sacroiliac joint (joint between a vertebrae and a pelvic bone), crest portions of right and left iliac regions (lateral side ends of the pelvic bone), and right and left spina iliac regions (front ends of the pelvic bone) of the wearer H.

Figure 8:
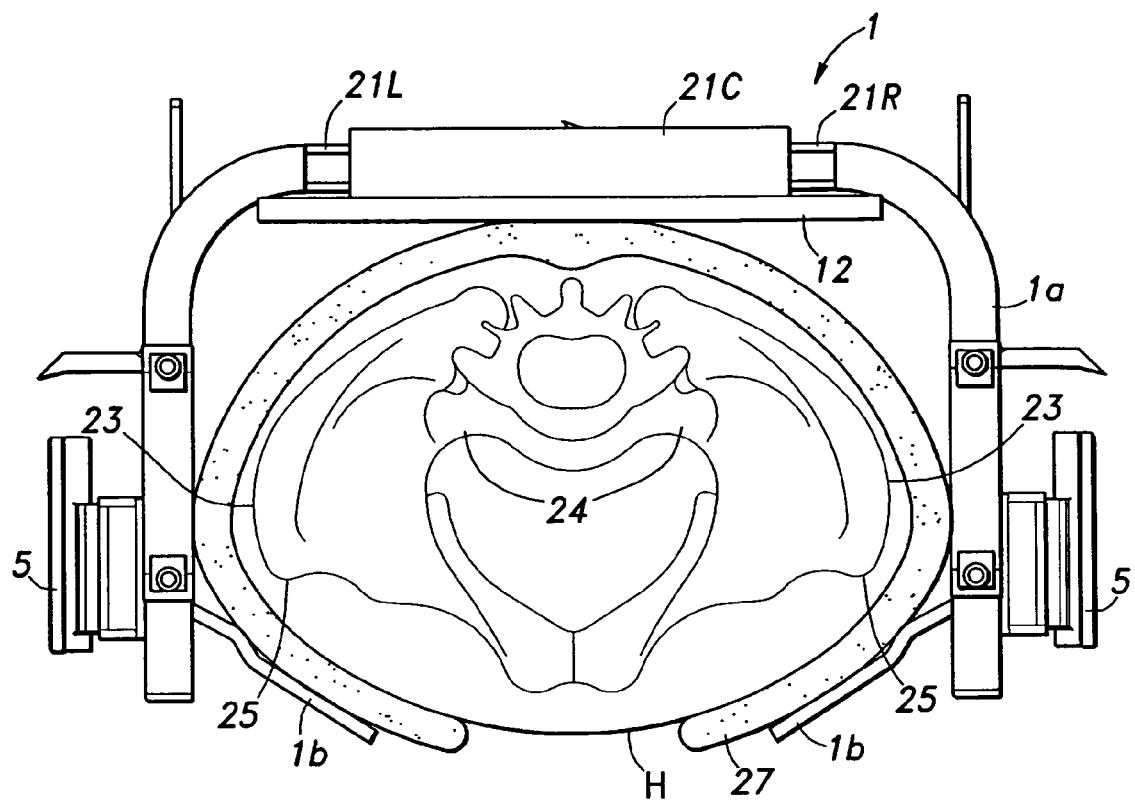
FIG. 8 is a view similar to FIG. 3 showing another modified embodiment of the present invention.

Alternatively, a one-piece cushioning pad 27 may be provided along the inner surface of the base portion 1a and flaps 1b as illustrated in FIG. 8. Such pads are effective in favorably distributing the load of the walking assistance device on the wearer, and accommodating the differences in the build of the wearer. This allows walking assistance devices of a same design and size to be comfortably worn by a large number of people, and this contributes to the reduction in the cost of the walking assistance device.

In the illustrated embodiment, the flaps 1b consist of separate members that are attached to the base portion 1a by using fasteners such as threaded bolts, a bonding agent or any known fastening means. However, it is also possible to form the base portion 1a and flaps 1b as an integral piece made of fiber-reinforced composite material. In such a case, the weight of the pelvis support member 1 can be reduced, and the load on the wearer can be minimized. Typically, the fiber-reinforced composite material is prepared by impregnating reinforcing fibers such as carbon fibers, glass fibers and aramid fibers with thermosetting plastic material such as epoxy, bismaleimide and phenol resins or thermoplastic plastic material such as PEEK, nylon-6, nylon-66 and polyethylene terephthalate resins. Also, when fiber-reinforced composite material is used, it is possible to increase the rigidity of the base portion 1a while increasing the flexibility of the flaps 1b by suitably selecting the orientation angle (relative to the circumferential direction), number of lamination layers and density of the reinforcing fibers.

Figure 9:
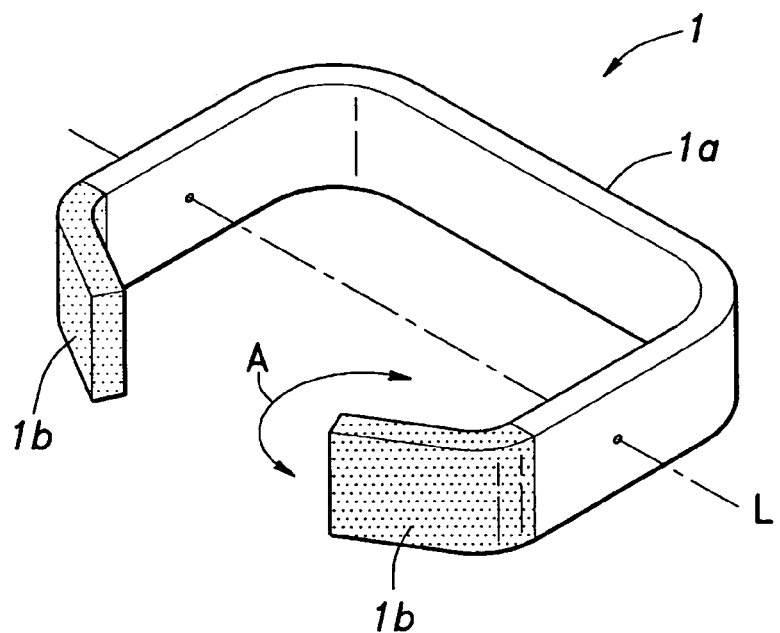
FIG. 9 is a simplified perspective view of the pelvis support member to illustrate the working principle of the present invention.

FIGS. 9 and 10 are schematic views of the walking assistance device illustrated in FIGS. 1 and 2 to show how the pelvis support member 1 can accommodate various sizes of different wearers owing to the use of the resilient flaps 1b in combination with the relatively rigid base portion 1a.

Referring to FIG. 9, the pelvis support member 1 consists of a substantially U-shaped base portion 1a and a pair of flaps 1b extending from either end of the base member 1a toward each other. Therefore, the pelvis support member 1 has a generally C-shaped configuration. In FIG. 10, the flaps 1b are indicated as shaded regions. When the walking assistance device is worn by the wearer, the back side of the wearer is engaged by the rear part of the base portion 1a and the front side of the wearer is engaged by the inner surfaces of the flaps 1b as illustrated in FIG. 10c.

The base portion 1a is given with a relatively high rigidity as discussed earlier. More specifically, the base portion 1a is given with a high rigidity against the torque applied to the base portion 1a around an imaginary line L that extends between the centers of the right and left hip actuators TA1. The base portion 1a is given with a rigidity which is adequate to support the reaction force of the hip actuators TA1 and keep the hip actuators TA1 fixed in pposition.

The flaps 1b are given with a high flexibility with respect to the inward and outward deflection thereof which is indicated by arrow A in FIG. 9. Therefore, when pushed outward by the wearer and the gap between the free ends of the flaps 1b is made greater than the width of the hip of the wearer, the flaps 1b permit the wearer to be admitted into the pelvis support member 1, and when pushed outward by the wearer, the flaps 1b permit the wearer to move out of the pelvis support member 1. The gap W1 between the free ends of the flaps 1b in an undeflected state is selected to be smaller that the width W2 of the hip U of the wearer so that the pelvis support member 1 is prevented from falling off from the wearer during the process of wearing the walking assistance device.

The process of wearing the walking assistance device is described in the following with reference to FIGS. 10a to 10c.

Figure 10A:
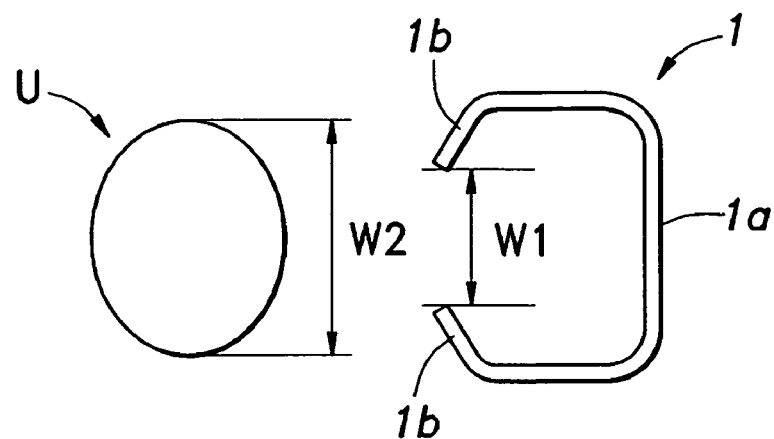
FIGS. 10a to 10c are simplified plan views showing how the pelvis support member is worn by the wearer.
Figure 10B:
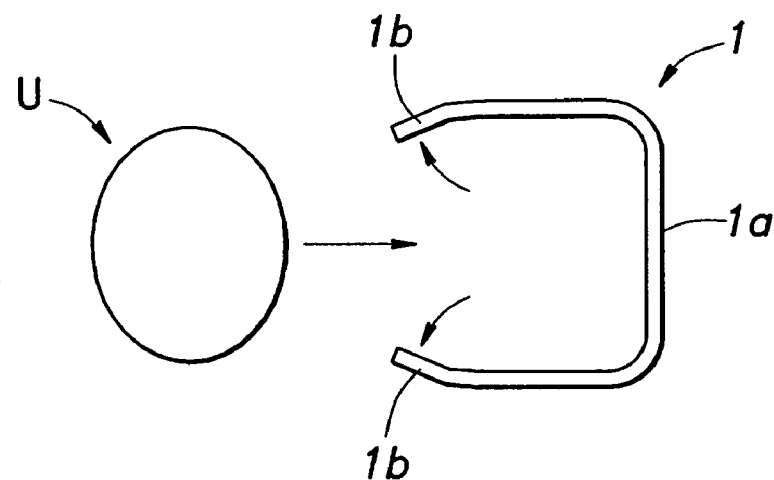
Figure 10C:
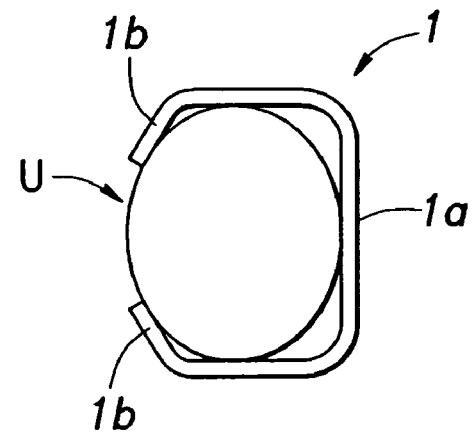

First of all, when the wearer is about to wear the walking assistance device, the gap W1 between the free ends of the flaps 1b is smaller that the width W2 of the hip U of the wearer as illustrated in FIG. 10a. When the flaps 1b are deflected outward by hands until the width between the free ends of the flaps 1b is increased to a value somewhat greater than W2 (the width of the hip U of the wearer), the hip U of the wearer is then passed into the pelvis support member 1 as illustrated in FIG. 10b. Because the flaps 1b are given with a high flexibility, the wearer can readily get into the pelvis support member 1 without regard to the size of the hip of the wearer. Once the hip U of the wearer is fully received in the pelvis support member 1, the flaps 1b are released and allowed to resiliently and lightly press upon the hip U of the wearer as illustrated in FIG. 10c. Also, because the flaps can accommodate the various builds and sizes of different wearers, the walking assistance devices of one size can fit a large number of people. Therefore, the walking assistance device is not required to be tailor-made, and there is no need to prepare the walking assistance devices of a large number of different sizes.

Although the present invention has been described in terms of preferred embodiments thereof, it is obvious to a person skilled in the art that various alterations and modifications are possible without departing from the scope of the present invention which is set forth in the appended claims.

The contents of the original Japanese patent applications on which the Paris Convention priority claim is made for the present application are incorporated in this application by reference.

The invention claimed is:

1. A walking assistance device that includes a pelvis support member adapted to be worn around a hip of a wearer and at least one actuator having a base end mounted on the pelvis support member and a free end engaging a thigh of the wearer, wherein:

the pelvis support member comprises a substantially U-shaped base portion having a relatively high rigidity and adapted to be worn around the hip of the wearer and a pair of flaps having a relatively high resilient flexibility and extending from either end of the base portion toward each other;

free ends of the flaps defining a gap smaller than a width of the hip of the wearer.

2. The walking assistance device according to claim 1, wherein the base portion and flaps are made of a single piece fiber-reinforced composite member.

3. The walking assistance device according to claim 1, wherein the flaps are made separately from the base portion and attached thereto by using a fastener or bonding agent.

4. The walking assistance device according to claim 1, wherein the base portion is provided with at least one slide guide that allows a lengthwise adjustment of the base portion and a locking arrangement for securing an adjusted state of the slide guide.

5. The walking assistance device according to claim 4, wherein the slide guide further includes a ratchet mechanism for selectively pulling together two ends of the slide guide in an incremental manner.

6. The walking assistance device according to claim 1, wherein the base portion is provided with a handle grip for holding the walking assistance device in a suspended state.

7. The walking assistance device according to claim 1, wherein the pelvis support member is adapted to engage the wearer at five points that include a back side of a sacroiliac joint (joint between a vertebrae and a pelvic bone), crest portions of right and left iliac regions (lateral side ends of the pelvic bone), and right and left spina iliac regions (front ends of the pelvic bone) of the wearer.

8. The walking assistance device according to claim 7, wherein a cushioning pad is interposed between at least one of the five points and the wearer.

* * * * *